United States Patent [19]
Lee et al.

[11] Patent Number: 5,824,689
[45] Date of Patent: Oct. 20, 1998

[54] QUINOLINE COMPOUND EXTRACTED FROM SCOLOPENDRA SUBSPINIPES, AND DERIVATIVES THEREOF

[75] Inventors: Ho-Seong Lee; Young-Jun Park; Min-Hwan Kim, all of Daejun; Seok-Shik Moon, Chungnam; Nam-Sun Cho, Chungbuk; Jong-Hyun Shin, Daejun; Young-Whan Suh, Kyungki-do; Jung-Ok Lee, Daejun, all of Rep. of Korea

[73] Assignee: Samsung General Chemicals Co., Ltd., Chungchungnam-do, Rep. of Korea

[21] Appl. No.: 865,126

[22] Filed: May 30, 1997

[30] Foreign Application Priority Data

May 31, 1996 [KR] Rep. of Korea ........................ 96-19136
Apr. 3, 1997 [KR] Rep. of Korea ........................ 97-12307

[51] Int. Cl.$^6$ ........................ A61K 31/47; C07D 215/24; C07D 215/20
[52] U.S. Cl. ............................................ 514/312; 546/153
[58] Field of Search .............................. 546/153; 514/312

[56] References Cited

PUBLICATIONS

Moon, J Nat Prod, vol. 59, pp. 777–779, Aug. 1996.
J. P. Michael; Quinoline, Quinazoline, and Acridone Alkaloids; pp. 163–172; vol. II, 1994.
James A. Matson & James A. Bush; The Journal of Antibiotics; vol. XLII No. 12; pp. 1763–1767; Sandramycin, A Novel Antitumor Antibiotic Produced by a Nocardioides SP, 1989.
James A. Matson et al.; The Journal of Antibiotics; vol. 46 No. I; pp. 162–166; Sandramycin, A Novel Antitumor Antibiotic Produced by a Nocardioides SP, 1993.

*Primary Examiner*—John Kight
*Assistant Examiner*—D. Margaret M. Mach
*Attorney, Agent, or Firm*—Bacon & Thomas

[57] ABSTRACT

The jineol extracted from scolopendra subspinipes is represented as the following formula (I):

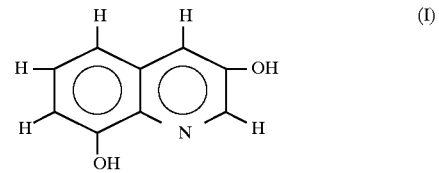

The jineol is obtained from scolopendra subspinipes by extracting scolopendra subspinipes with a solvent, separating an activating portion from the extracted liquid with an organic solvent, and purifying an anticancerous activating portion from the activating portion by chromatography.

The jineol derivatives prepared from the jineol extracted scolopendra subspinipes are represented as the following formula (II):

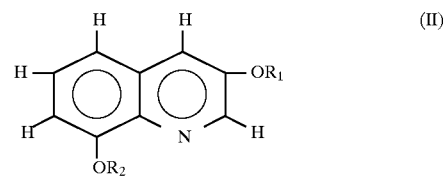

wherein each $R_1$ and $R_2$, independently of each other, is a hydrogen; a lower alkyl group of $C_1$ to $C_6$; a cycloalkyl group of $C_5$ to $C_7$ having a substituting group; an alkyl group of $C_1$ to $C_4$ having a phenyl group with one to three substituting groups; a lower alkyl group of $C_1$ to $C_6$ having a hydroxy, an alkoxy having $C_1$ to $C_5$, or an aryloxy; a lower acyl group of $C_1$ to $C_7$ having a hydroxy, an alkoxy having $C_1$ to $C_5$, or an aryloxy; a cycloalkylcarbonyl group of $C_5$ to $C_7$ with one to three substituting groups; or an acyl group of $C_1$ to $C_4$ having a phenyl group with one to three substituting groups.

20 Claims, 8 Drawing Sheets

QUINOLINE COMPOUND EXTRACTED FROM SCOLOPENDRA SUBSPINIPES, AND DERIVATIVES THEREOF

FIELD OF THE INVENTION

The present invention relates to a novel quinoline compound which is extracted from scolopendra subspinipes, which will be called as "jineol" hereinafter, and to a method for extracting jineol from scolopendra subspinipes. The present invention relates to derivatives of jineol, which are prepared from jineol. This invention also includes a method to synthesize jineol and derivatives thereof. This invention further relates to a use of jineol and derivatives thereof for anticancer treatment, and a pharmaceutical composition using jineol or derivatives thereof.

BACKGROUND OF THE INVENTION

Scolopendra subspinipes have been traditionally used for treating a febrile seizure, a malignant tumor, a neuralgia or a diphtheria in oriental countries, and particularly the powder of dry scolopendra subspinipes has been used for the purpose above (Bensky, D; Gamble, A.. *Chinese Herbal Medicine MATBRIA MEDICA; Bastland Press, Inc.*: Seattle, Wash., 1986; pp 612–613). Notwithstanding the pharmaceutical effect of scolopendra subspinipes, the components of scolopendra subspinipes and pharmaceutical functions thereof have not been researched specifically yet.

The inventors of this invention have extracted a novel quinoline compound from scolopendra subspinipes, and found that the extracted quinoline compound has a cytotoxicity to a cancerous cell.

Quinoline alkaloids having an oxygen atom at 3-carbon position are rare in the nature (Michael, J. P. Nat. Prod, Rep. 1994. 11. 163–172). It is known that a cyclic peptide structure of 3-hydroxy quinoline has an anticancer activity and also 3-hydroxy quinoline-2-carboxylic acid can be obtained from a microorganism. The another example is sandramycin which has been discovered as anticancer agent (Matson, J. A; Bush, J. A. J. Antibiot. 1989, 42, 1763–1767 and Matson, J. A.; Colson, K. L.; Belofsky, D. N.; Bleiberg, B. B. J. Antibiot. 1993, 46, 162–166). However, jineol of this invention is a new 3-hydroxy quinolinic compound that has not been discovered yet.

The amount of jineol extracted from scolopendra subspinipes is very limited for commercial use. Accordingly, the present inventors have developed methods for synthesizing jineol and derivatives thereof which have anticancer activities.

OBJECTS OF THE INVENTION

An object of the present invention is to provide jineol having an anticancer activity, which is extracted from scolopendra subspinipes.

Another object of the present invention is to provide a method for extracting jineol from scolopendra subspinipes.

A further object of the present invention is to provide jineol derivatives prepared from the jineol extracted from scolopendra subspinipes.

A further object of the present invention is to provide a method for preparing jineol derivatives from the jineol extracted from scolopendra subspinipes.

A further object of the present invention is to provide a method for synthesizing jineol and jineol derivatives which have an anticancer activity.

A still further object of the present invention is to provide a pharmaceutical composition using jineol or jineol derivatives above.

The foregoing and other objects of the present invention will be achieved in the following description.

SUMMARY OF THE INVENTION

Jineol extracted from scolopendra subspinipes in accordance with the present invention is represented as the following formula (I):

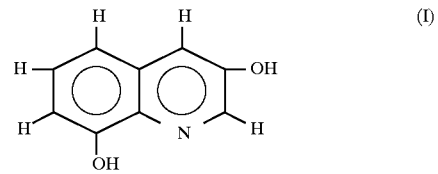

Jineol is obtained from scolopendra subspinipes by extracting scolopendra subspinipes with a solvent, separating an activating portion from the extracted liquid with an organic solvent, and purifying an anticancerous activating portion from the activating portion by chromatography.

Jineol derivatives prepared from the jineol extracted scolopendra subspinipes are represented as the following formula (II):

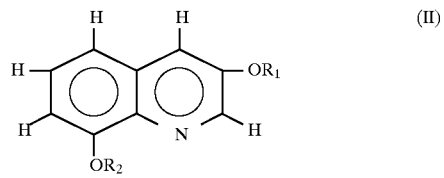

wherein each $R_1$ and $R_2$, independently of each other, is a hydrogen; a lower alkyl group of $C_1$ to $C_6$; a cycloalkyl group of $C_5$ to $C_7$ having a substituting group; an alkyl group of $C_1$ to $C_4$ having a phenyl group with one to three substituting groups; a lower alkyl group of $C_1$ to $C_6$ having a hydroxy, an alkoxy having $C_1$ to $C_5$, or an aryloxy; a lower acyl group of $C_1$ to $C_7$ having a hydroxy, an alkoxy having $C_1$ to $C_5$, or an aryloxy; a cycloalkylcarbonyl group of $C_5$ to $C_7$ with one to three substituting groups; or an acyl group of $C_1$ to $C_4$ having a phenyl group with one to three substituting groups.

In formula (II), it is preferable that each $R_1$ and $R_2$, independently of each other, is selected from the group consisting of a hydrogen, a methyl group and an acetyl group.

The jineol of formula (I) or jineol derivatives of formula (II) can provide a pharmaceutical composition that shows an anticancer activity.

For synthesizing the jineol of formula (I) or jineol derivatives of formula (II), the compound of the following formula (III), which is known already, is used as a starting material:

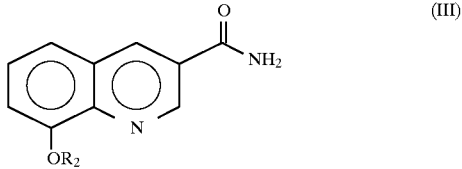

wherein $R_2$ is the same as defined above.

The jineol of formula (I) or jineol derivatives of formula (II) are synthesized by Hoffmann rearrangement of the known compound of formula (III) and then diazotization in an acidic medium followed by dealkylation, alkylation or acylation.

BRIEF DESCRIPTION OF THE DRAWINGS

The present invention will be more fully understood by reference to the following detailed description of the preferred embodiment of the present invention when read in conjunction with the accompanying drawings.

DETAILED DESCRIPTION OF THE INVENTION

Jineol extracted from scolopendra subspinipes in accordance with the present invention is represented as the following formula (I):

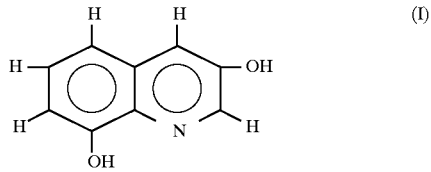

Jineol of this invention is a new 3-hydroxy quinolinic compound that had neither been discovered nor synthesized yet.

The method of obtaining jineol from scolopendra subspinipes comprises extracting scolopendra subspinipes with a solvent, separating an activating portion from the extracted liquid with an organic solvent, and purifying an anticancerous activating portion from the activating portion by chromatography.

At the step of extracting, methanol or ethanol can be used as solvent. Scolopendra subspinipes are extracted with methanol or ethanol and the extracted liquid is concentrated.

At the step of separating, the extracts are separated with an organic solvent through a layer separation. In other words, the extracts are purified through a layer separation. It is preferable that the layer separation is carried out twice. The first layer separation is to separate polar portion from the non-polar impurities of the extracts. Hexane and aqueous methanol may be used as organic solvent in the first layer separation. The polar portion which has been separated through the first layer separation is separated into a portion of polar impurities and activating portion through the second layer separation. Water and ethyl acetate may be used together as organic solvent in the second layer separation. Chloroform may be used instead of ethyl acetate.

At the third step of purifying, an anticancerous activating portion is obtained from the activating portion by chromatography. Silicagel chromatography or LH-20 chromatography can be applied in the third step, or both of these can be applied. Hexane and ethyl acetate are used together as the eluent in silicagel chromatography. The activating portion of the extracts is purified by silicagel chromatography. For further purification, HL-20 chromatography is followed. Methanol or methanol/ethyl acetate mixed solution can be used as eluent.

After the third step by the chromatography, the novel compound of formula (I) is obtained, which is yellow-red or dark yellow-red colored solid.

The chemical formula of jineol is found out by spectroscopic analyses. An NMR spectroscope, an infrared spectroscope and an ultraviolet spectroscope are utilized for spectroscopic analyses of jineol.

Figure 1:
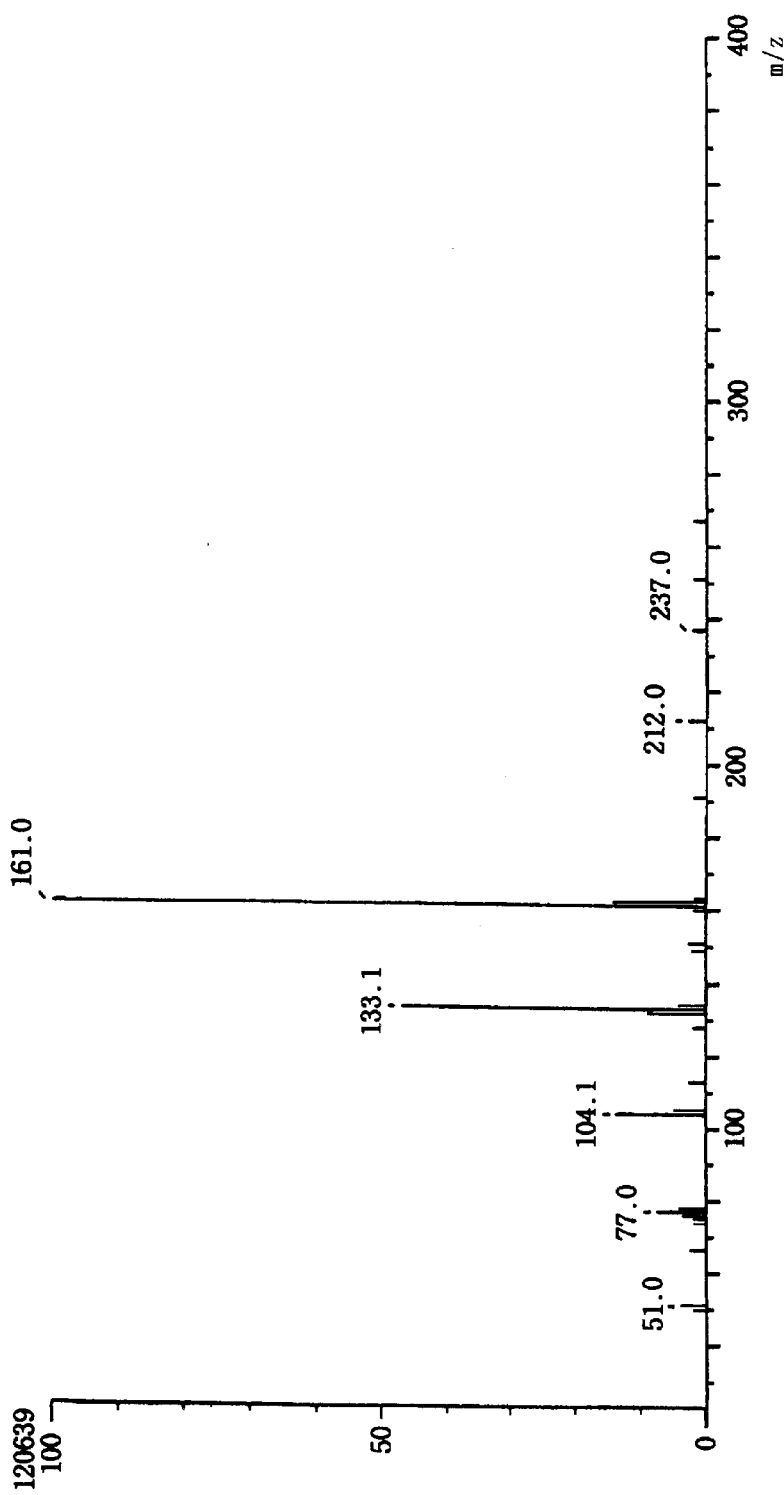
FIG. 1 is a mass spectrum of 3,8-dihydroxy quinoline extracted from scolopendra subspinipes in accordance with the present invention.

The molecular weight of jineol is 161 as measured by an electron collision or electron emission mass analysis. FIG. 1 is a mass spectrum of 3,8-dihydroxy quinoline extracted from scolopendra subspinipes in accordance with the present invention. The molecular formula of jineol is found out as $C_9H_7NO_2$ by a high resolution mass spectrum.

Figure 2:
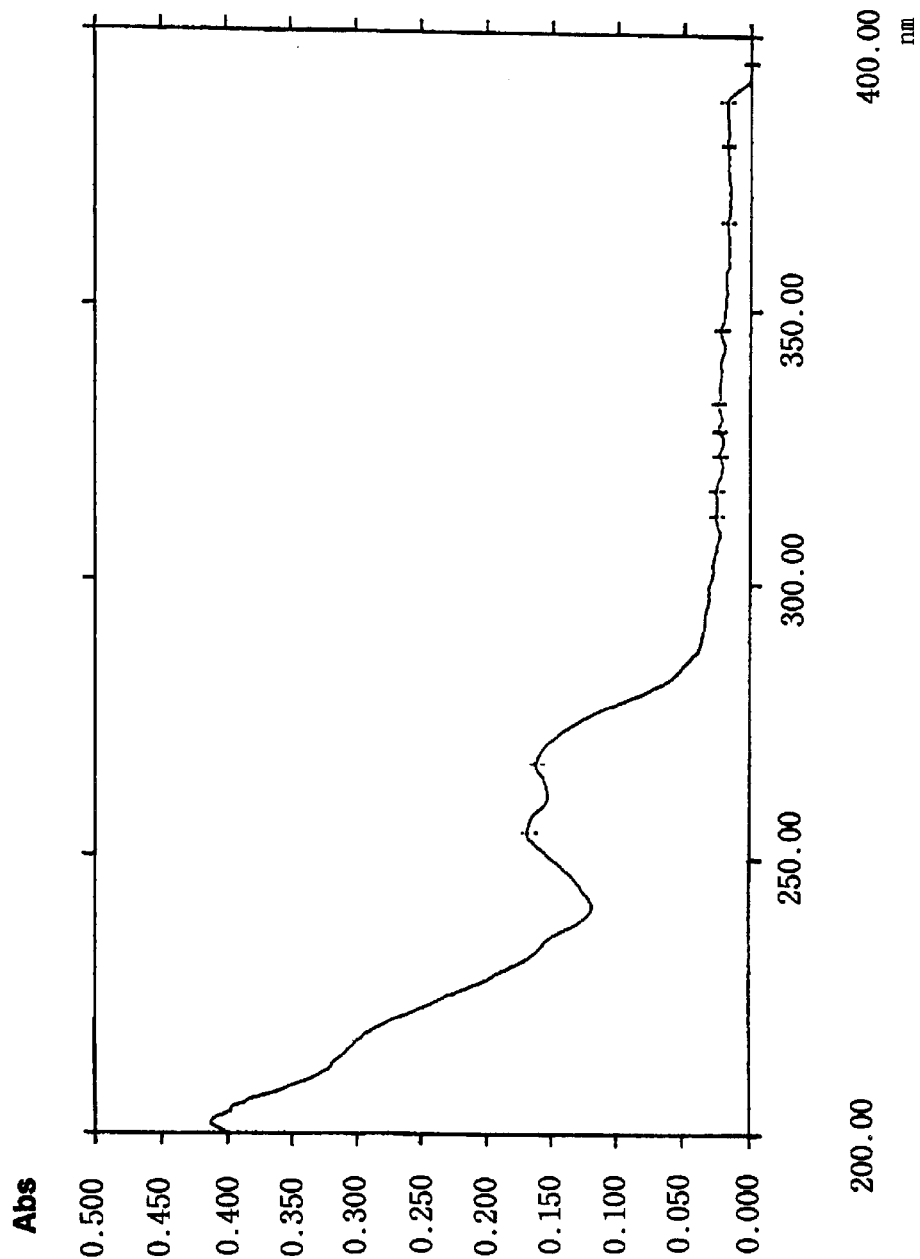
FIG. 2 is an ultraviolet spectrum of 3,8-dihydroxy quinoline extracted from scolopendra subspinipes in accordance with the present invention.

FIG. 2 is an ultraviolet spectrum of 3,8-dihydroxy quinoline extracted from scolopendra subspinipes in accordance with the present invention. The spectrum shows peaks of absorption at 254 nm and 267 nm.

Figure 3:
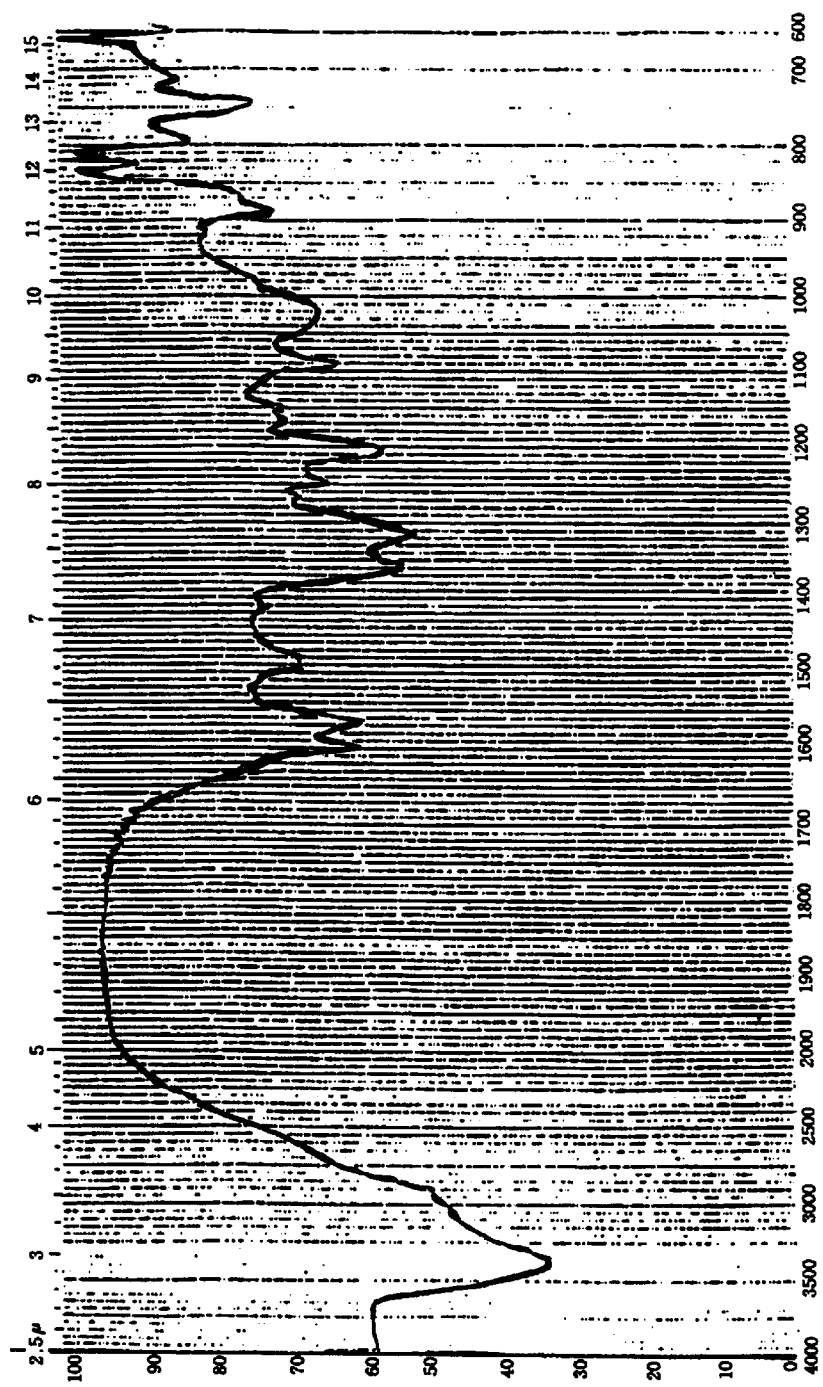
FIG. 3 is an infra-red spectrum of 3,8-dihydroxy quinoline extracted from scolopendra subspinipes in accordance with the present invention.

FIG. 3 is an infrared spectrum of 3,8-dihydroxy quinoline extracted from scolopendra subspinipes in accordance with the present invention. The spectrum shows characteristic absorptions at 3370, 1594, 1562, 1355, 1313 and 1200 cm$^{-1}$. This suggests that jineol comprises a hydroxy quinoline.

Figure 4:
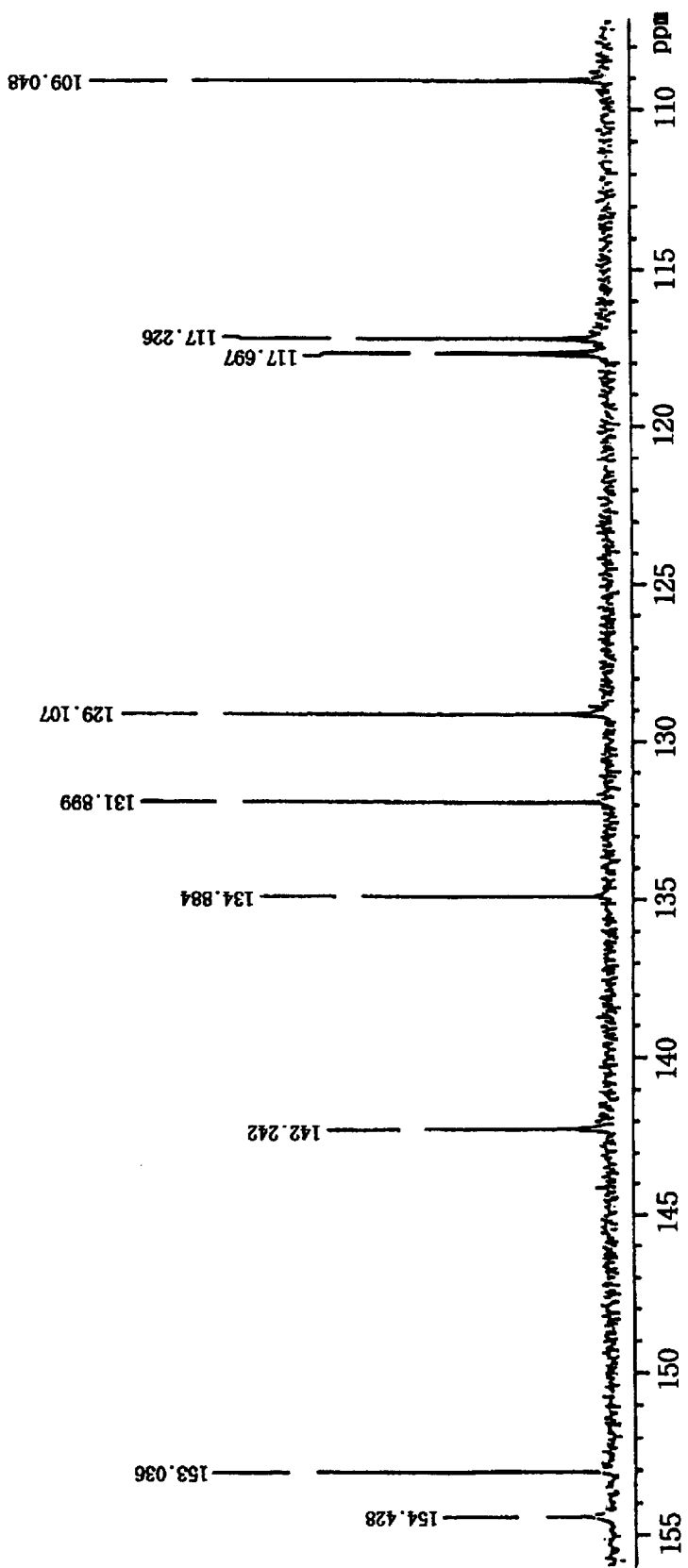
FIG. 4 is a $^{13}$C NMR spectrum of 3,8-dihydroxy quinoline extracted from scolopendra subspinipes in accordance with the present invention.

FIG. 4 is a $^{13}$C NMR spectrum of 3,8-dihydroxy quinoline extracted from scolopendra subspinipes in accordance with the present invention. The spectrum shows that the compound has 9 aromatic carbon atoms.

Figure 5:
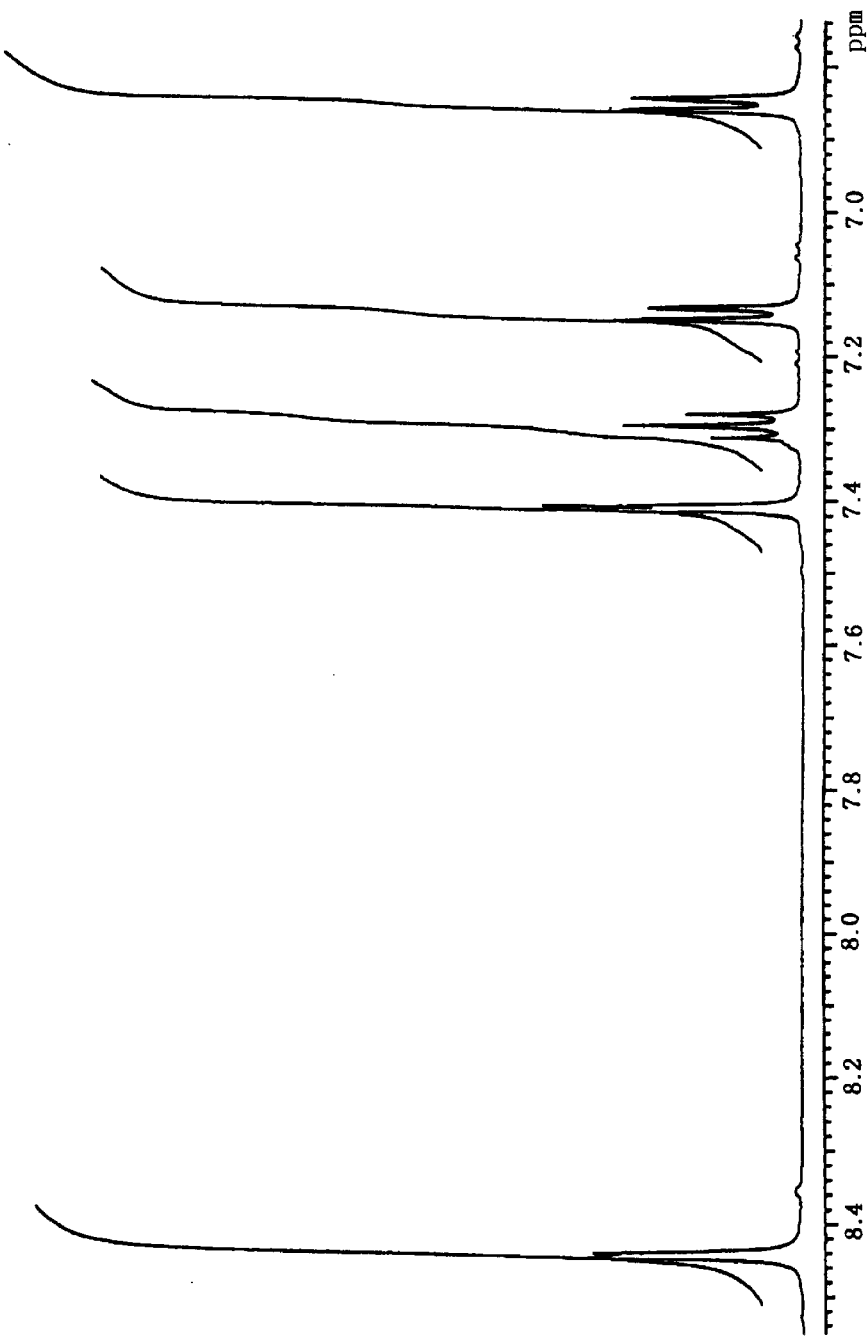
FIG. 5 is a $^1$H NMR spectrum of 3,8-dihydroxy quinoline extracted from scolopendra subspinipes in accordance with the present invention.
Figure 6:
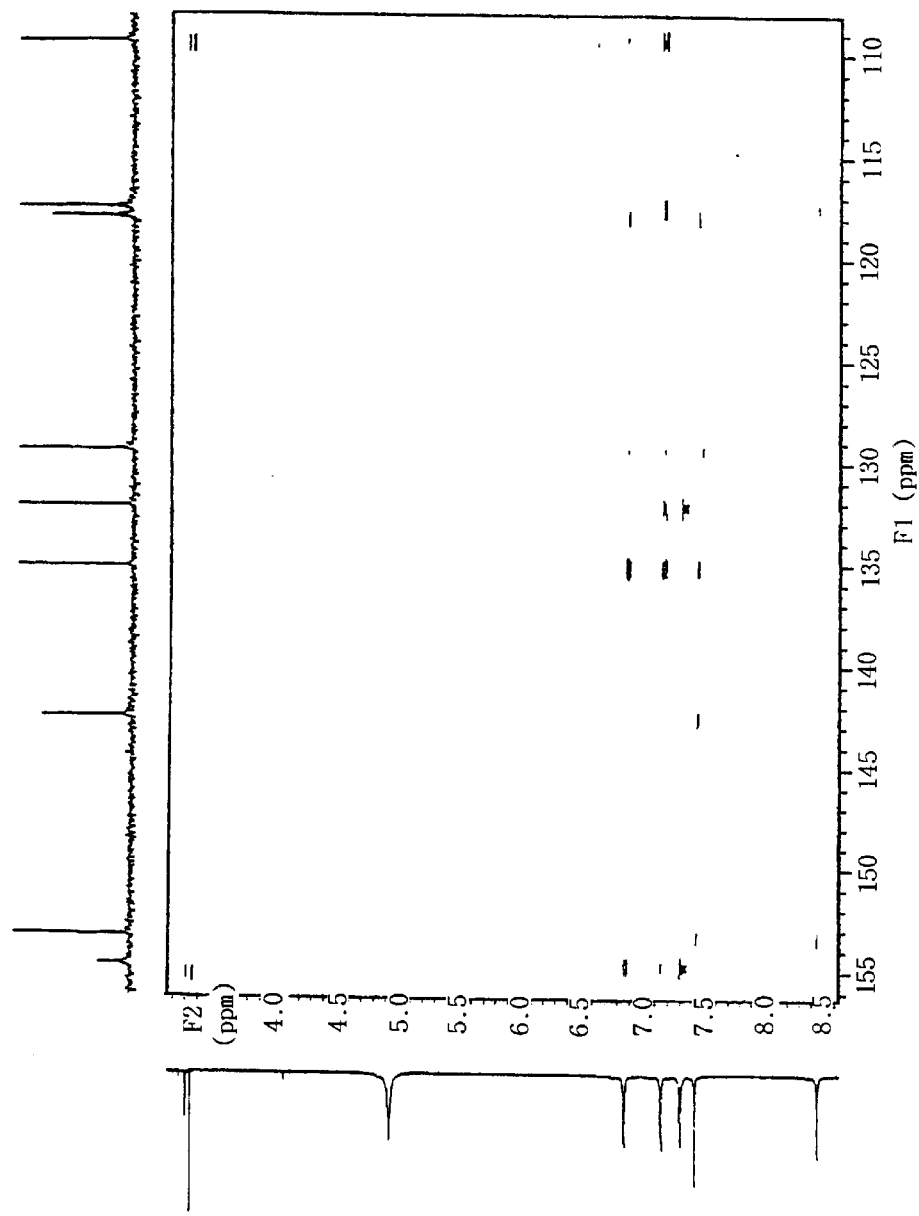
FIG. 6 is an HMBC spectrum of 3,8-dihydroxy quinoline extracted from scolopendra subspinipes in accordance with the present invention.

FIG. 5 is a $^1$H NMR spectrum of 3,8-dihydroxy quinoline extracted from scolopendra subspinipes in accordance with the present invention. Methine protons appear as H-2, H-4, H-5, H-6 and H-7 by $H_1$, H-COSY and HMQC experiments. Methine proton (d, J=2.5 Hz) of δ8.44 ppm is coupled with methine proton (d, J=2.5 Hz) of δ7.14 ppm which is weakly coupled with methine proton of δ7.14 ppm. Methine proton (d, J=8.0 Hz) of δ7.14 ppm is coupled with methine proton (d, J=8.0 Hz) of δ7.29 ppm which is strongly coupled with methine proton (d, J=8.0 Hz) of δ6.85 ppm. The positions of carbons are decided by HMBC and NOE (nuclear overheuser effect) experiments. By the HMBC experiment, C-3 of δ153.0 ppm shows relationship with H-2 (δ8.44) and H-4 (δ7.41), C-8 of δ154.4 ppm shows relationship with H-6 (δ7.29) and H-7 (δ6.85). By the NOE experiment, a nuclear overheuser effect is strongly shown between H-4 and H-5. FIG. 6 is an HMBC spectrum of 3,8-dihydroxy quinoline extracted from scolopendra subspinipes in accordance with the present invention.

Various jineol derivatives are prepared from jineol that is extracted from scolopendra subspinipes. The jineol derivatives are represented as the following formula (II):

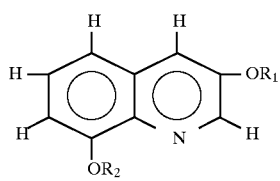

(II)

wherein each $R_1$ and $R_2$, independently of each other, is a hydrogen; a lower alkyl group of $C_1$ to $C_6$; a cycloalkyl group of $C_5$ to $C_7$ having a substituting group; an alkyl group of $C_1$ to $C_4$ having a phenyl group with one to three substituting groups; a lower alkyl group of $C_1$ to $C_6$ having a hydroxy, an alkoxy having $C_1$ to $C_5$, or an aryloxy; a lower acyl group of $C_1$ to $C_7$ having a hydroxy, an alkoxy having $C_1$ to $C_5$, or an aryloxy; a cycloalkylcarbonyl group of $C_5$ to $C_7$ with one to three substituting groups; or an acyl group of $C_1$ to $C_4$ having a phenyl group with one to three substituting groups.

In formula (II), it is preferable that each $R_1$ and $R_2$, independently of each other, is selected from the group consisting of hydrogen, a methyl group and an acetyl group.

Figure 7:
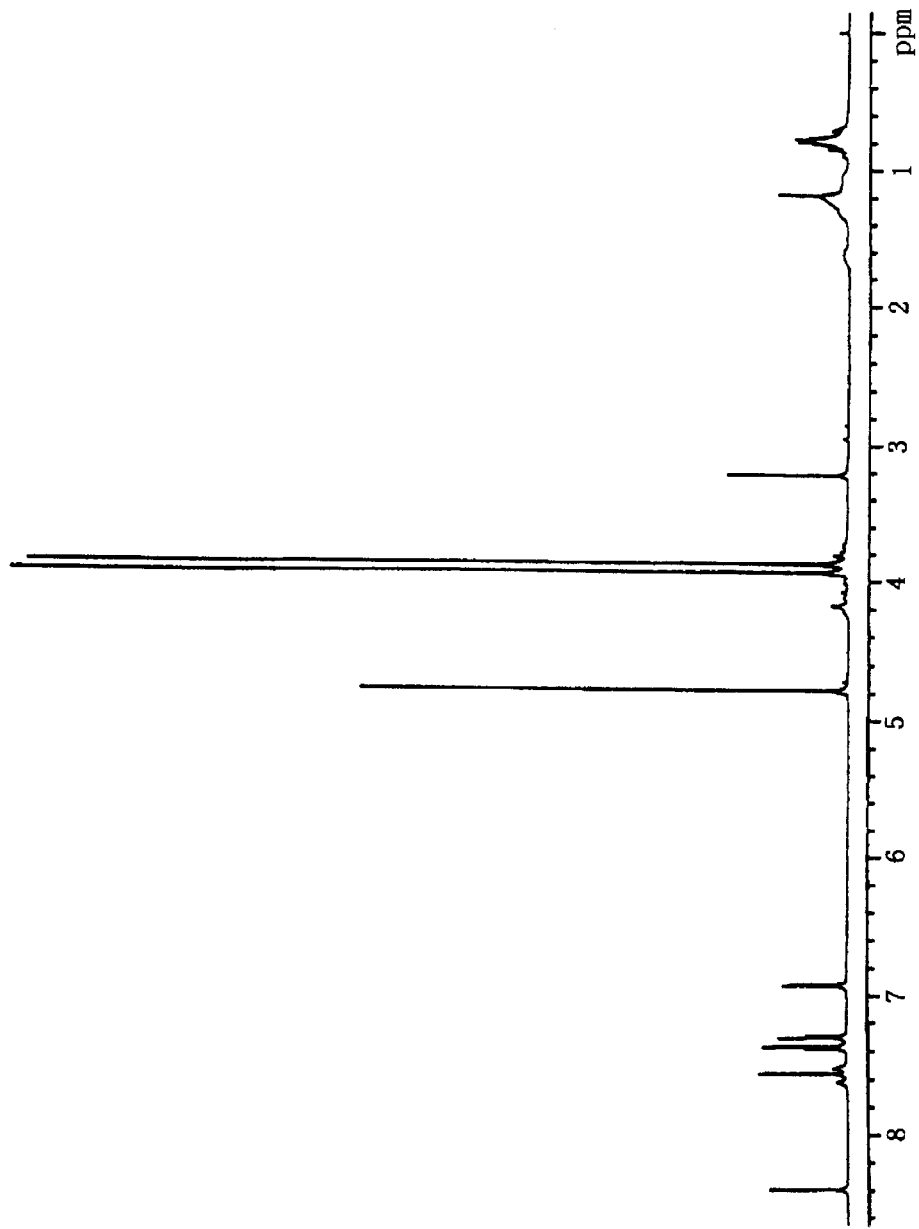
FIG. 7 is a $^1$H spectrum of 3,8-dimethoxy quinoline in accordance with the present invention.

The jineol derivative in formula (II) wherein $R_1$ and $R_2$ are methyl groups is prepared using diazomethane. FIG. 7 is a $^1$H spectrum of 3,8-dimethoxy quinoline in accordance with the present invention. In 3,8-dimethoxy quinoline, when H-7 is irradiated a nuclear overheuser effect is observed at 8-methoxy hydrogen of δ4.02 ppm and at H-6 of δ7.46 ppm. Also, a nuclear overheuser effect is observed at 3-methoxy hydrogen of δ3.95 ppm and at H-5 of δ8.48 ppm when H-4 is irradiated.

Figure 8:
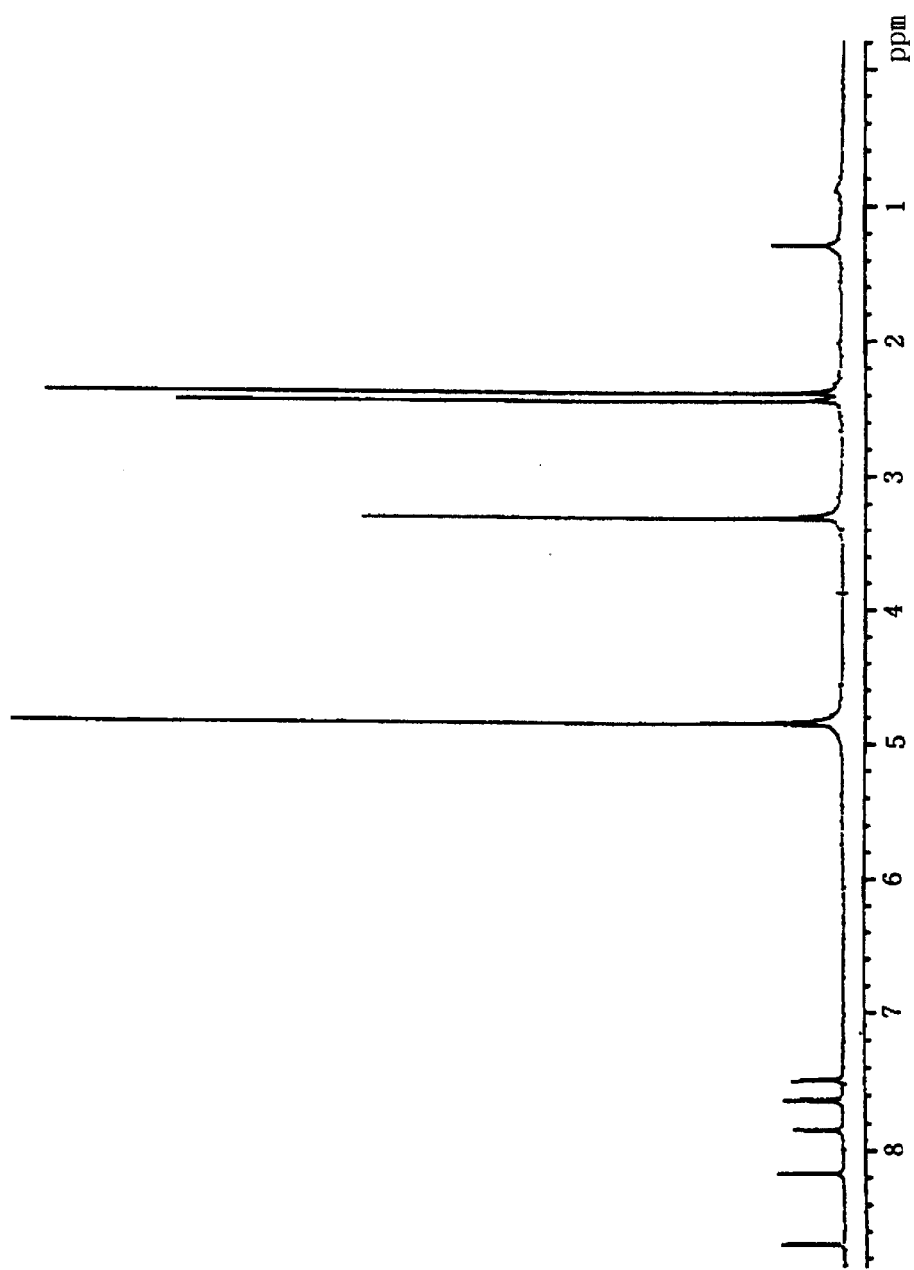
FIG. 8 is a $^1$H spectrum of 3,8-diacetoxy quinoline in accordance with the present invention.

The jineol derivative in formula (II) wherein R1 and R2 are acetyl groups is prepared using acetic anhydride. FIG. 8 is a $^1$H spectrum of 3,8-diacetoxy quinoline in accordance with the present invention.

Jineol of formula (I) or jineol derivatives of formula (II) have an anticancer activity. Jineol compounds show an anticancer activity to the cells such as A-549 non-small cell lung cancer, SKOV-3 ovarian cancer, SK-Mel-2 melanoma, XP-498 central nerve system cancer and HCT-15 colon cancer. Accordingly, jineol or jineol derivatives can provide a pharmaceutical composition having anticancer activity. Jineol or jineol derivatives can be used for preparing a pharmaceutical composition for anticancer along with a pharmaceutically acceptable carrier and other pharmaceutically acceptable additives.

For synthesizing the jineol of formula (I) or jineol derivatives of formula (II), the compound of formula (III) below is used as starting material. The preparation method of formula (III) is known already (Journal of Medicinal Chemistry, 1979, Vol. 22, No. 7, pp 816–823). The compound of formula (III) is prepared by the following reaction paths:

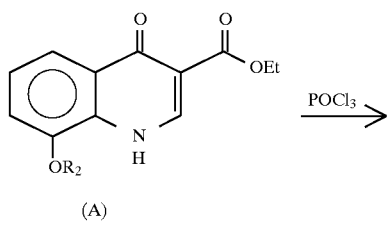

(A)

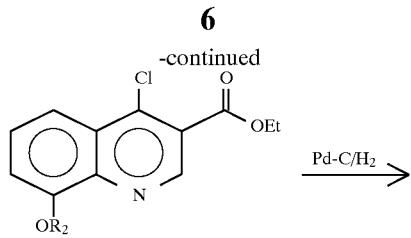

(B)

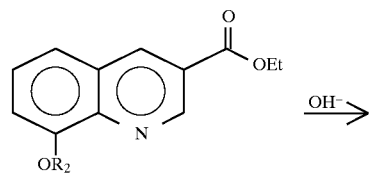

(C)

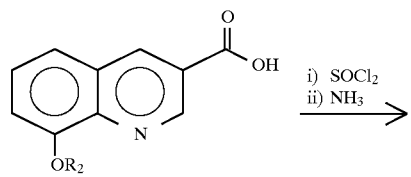

(D)

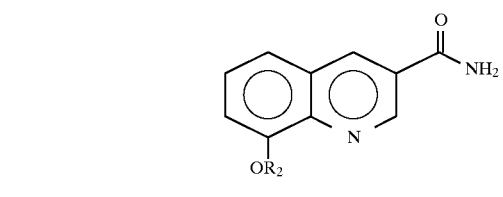

(III)

wherein $R_2$ is the same as defined above.

As shown in the reaction paths above, compound (B) is produced reacting compound (A) with a phosphorous oxychloride, compound (C) is produced by reacting the compound (B) with hydrogen gas in Pd catalyst, compound (D) is produced by reacting the compound (C) by a hydrolysis in an alkali state, and compound (III) is finally obtained by reacting the compound (D) with a thionyl chloride followed by adding ammonia gas.

Jineol and jineol derivatives are synthesized from the compound of formula (III). The general formula (II) of jineol or jineol derivatives is prepared by the following reaction paths:

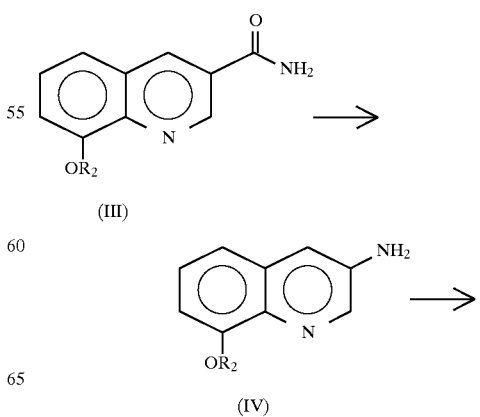

(III)

(IV)

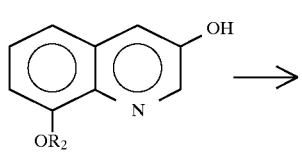

(V)

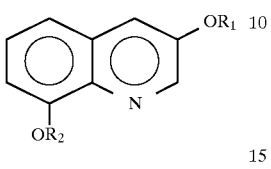

(II)

The jineol of formula (I) or jineol derivatives of formula (II) are synthesized by Hoffmann rearrangement of the known compound of formula (III) and then diazotization in an acidic medium followed by dealkylation, alkylation or acylation.

The jineol extracted from scolopendra subspinipes is represented as the following formula (I), and is wherein $R_1$ and $R_2$ of formula (II) are hydrogen atoms. The jineol of formula (I) is prepared by dealkylation of 3-hydroxy-8-methoxy quinoline of compound (V) wherein $R_2$ is a methyl group. The reaction is as follow:

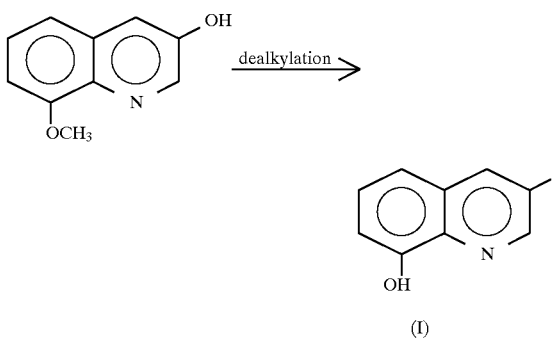

One of jineol derivatives, 3,8-dimethoxy quinoline, is a compound of formula (II) in which $R_1$ and $R_2$ are methyl groups. The jineol derivative, 3,8-dimethoxy quinoline, is prepared by alkylation of 3-hydroxy-8-methoxy quinoline of compound (V) wherein $R_2$ is a methyl group. The reaction is as follow:

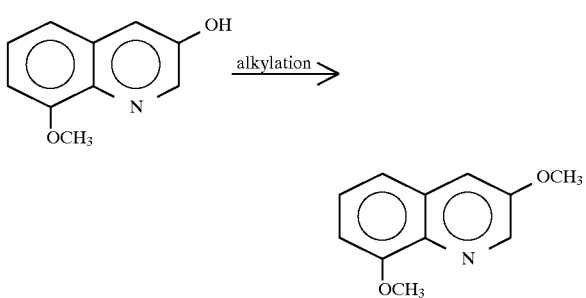

Another jineol derivative, 3-acetoxy-8-methoxy quinoline, is a compound of formula (II) in which $R_1$ is an acetyl group and $R_2$ is a methyl group. The jineol derivative, 3-acetoxy-8-methoxy quinoline, is prepared by acylation of 3-hydroxy-8-methoxy quinoline of compound (V) wherein $R_2$ is a methyl group. The reaction is as follow:

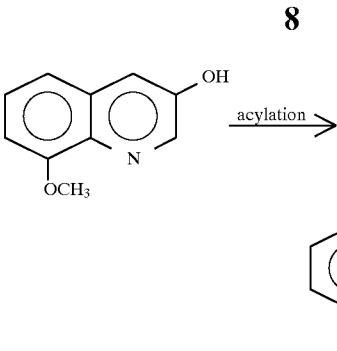

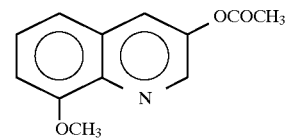

The invention may be better understood by reference to the following examples which are intended for purpose of illustration and are not to be construed as in any way limiting the scope of the present invention, which is defined in the claims appended.

EXAMPLES

Extraction of Jineol from Scolopendra Subspinipes

Jineol was extracted from scolopendra subspinipes in accordance with the following example 1.

Example 1

Scolopendra subspinipes of 3.1 g was extracted twice with 200 ml of methanol. The combined extracts were concentrated and layer-separated with hexane and methanol. The methanol layer was concentrated and layer-separated with water and ethyl acetate. The ethyl acetate layer was concentrated and the resulting residue was purified with silicagel chromatography by gradient elution of 1:1 hexane/ethyl acetate to ethyl acetate. The anticancer activity was measured by SRB assay. The portion activated by the SRB assay was concentrated and purified by LH-20 chromatography eluting with methanol. The activated portion was concentrated and jineol of 2 mg was obtained.

The spectroscopic properties of the jineol are as follow: yellow-red or dark yellow-red color; mp 139°–141° C.; BMIS m/z 161(100), 133(47), 104(14); HRBIMS m/z 161.0485; (−) ESMS m/z 160 [M-H]; IR(KBr) νmax 3370, 1595, 1562, 1355, 1313, 1200, 1087, 885 and 743 $cm^{-1}$; UV(MeOH) λ ... 254, 267 nm; $^1$H NMR δ8.44(1H, d, J=2.5 Hz, H-4), 7.29(1H, t, J=8.0Hz, H-6), 7.14(1H, d, J=8.0Hz, H-5) 6.85(1H, d, H=8.0 Hz, H-7)ppm; $^{13}$C NMR δ154.4(C, C-8), 153.0(C, C-3), 142.2(CH, C-4), 134.9(C,C-8a), 131.9 (C, C-4a), 129.1(CH, C-6), 117.7(CH, C-5), 117.2(CH, C-4) and 109.1(CH, C-7)ppm; HMBC correlations: C-2 and H-4; C-3 and H-2, H-4: C-4 and H-5, H-6; C-5 and H-5; C-8 and H-7; C-8a and H-4, H-5, H-7.

Preparation of Jineol Derivatives

Example 2

Jineol of 4.5 mg was dissolved in 2 ml of ethanol, and diazomethane ether solution was slowly dropped to the solution. After the excess of diazomethane and solvent was removed by purging with nitrogen gas, the solution was purified by silicagel chromatography to give 4.2 mg of 3,8-dimethoxy quinoline with 80% yield.

The spectroscopic properties of the jineol are as follow: UV(MeOH) λ ... 210, 250 nm; $^1$H NMR δ8.48(1H, d, J=2.6 Hz, H-2), 7.64(1H, d, J=2.6 Hz, H-4), 7.46(1H, t, J=7.9 Hz, H-6), 7.38(1H, dd, J=7.9, 1.0 Hz, H-5), 7.02(1H, dd, J-7.9, 1.0 Hz, H-7), 4.02(3H, s, 8-$OCH_8$), 3.95(3H, 8, 3-$OCH_8$) ppm.

Example 3

Jineol of 5.0 mg was dissolved in 0.5 ml of acetic acid anhydride and 0.5 ml of pyridine, and then the solution was agitated at room temperature for 9 hours. After the solution was diluted with ethyl acetate, it was washed with sodium dicarbonate solution and brine. The solution was dried with anhydrous magnesium sulfate anhydride. After the residue was removed, the solution was purified by silicagel chromatography to give 5.9 mg of 3,8-diacetoxy quinoline with 78% yield.

The spectroscopic properties of the jineol are as follow: mp 101°–102° C.; UV(MeOH) λ . . . 212, 253 nm; $^1$H NMR δ8.69(1H, d, J=2.6 Hz, H-2), 8.16(1H, d, J=2.6 Hz, H-4), 7.85(1H, dd, J=7.9 1.5 Hz, H-7), 7.63(1H, t, J=7.9, Hz, H-6), 7.48(1H, dd, J=7.9, 1.5 Hz, H-5), 2.44(3H, s, 8-OCOCH$_8$), 2.38(3H, s, 3-).

Anticancer Activity Test

The anticancer activities of the jineol and derivatives thereof of examples 1 to 5 were tested by the SRB assay (Skehan, P.: Storeng, R.; Scudiero, D.; Monks, A.; McMahon, J.; Vistoca, D.; Warren, J. T.; Bokesch, H.; Kenny, S.; Boyd, M. R.; J. Natl. Cancer Inst. 1990, 82, 1107–1112 and Rubinstein, L. V.; Shoemaker, R. H.; Paull, K. D.; Simon, R. M.; Tosini, S.; Skehan, P.; Scudiero, D. A.; Monks, A.; Boyd, M. R.; J. Natl. Cancer Inst. 1990, 82, 1113–1118) for A-509 non-small cell lung cancer, SKOV-3 ovarian cancer, SK-Mel-2 melanoma, XP-498 central nerve system cancer and HCT-15 colon cancer. The cytotoxicities of examples 1–5 as well as platinum-containing anticancer agents such as carboplatin, cisplatin and adriamycin were shown in Table 1. From Table 1, it is apparent that the jineol and derivatives thereof according to the present invention are superior to the conventional platinum-containing anticancer agents.

TABLE 1

| | ($BD_{60}$ μg/ml) | | | | |
| --- | --- | --- | --- | --- | --- |
| | human cell* | | | | |
| | A-549 | SKOV-3 | SK-Mel-2 | XP-498 | HCT-15 |
| example 1 | 5.8 | 4.5 | 5.6 | 10 | 1.9 |
| example 2 | 38 | 32 | 21 | 29 | 42 |
| example 3 | 8 | 14 | 11 | 12 | 8 |
| carboplatin | 22 | 13 | 10 | 13 | 47 |
| cisplatin | 0.99 | 0.99 | 0.73 | 0.36 | 1.39 |
| adriamycin | 0.05 | 0.11 | 0.05 | 0.1 | 1.77 |

*
A-509: non-small cell lung cancer,
SKOV-3: ovarian cancer,
SK-Mel-2: melanoma,
XP-498: central nerve system cancer, and
HCT-15: colon cancer.

Synthesis of Jineol and its Derivatives

Example 4

Synthesis of Jineol (3,8-Dihydroxy Quinoline)

(1) Preparation of 3-Amino-8-Methoxy Quinoline [Compound (IV)]

Sodium hydroxide of 17.6 g was dissolved in 600 ml of water, and the solution was cooled to 0° C. To the solution was added 7.2 ml of bromine, and 23.2 g of 8-methoxy quinoline-3-carboxylamide [compound (III)] was added at 0° to 5° C. After the solution was agitated for 1 hour at the temperature, and agitated for an additional 1 hour at room temperature. The solution was heated to 80° C., agitated for 10 minutes, and cooled to room temperature. The solution was saturated with sodium chloride and then extracted with dichloromethane. The resulting extract was dried with anhydrous magnesium sulfate anhydride. The dichloromethane was removed by vacuum distillation. 12.7 g of 3-amino-8-methoxy quinoline [compound (IV)], which is dark yellow, was obtained in a solid state.

The spectroscopic property of the compound is as follow: $^1$H-NMR(CDCl$_3$)δ(ppm): 8.49(1H, d, H-2), 7.34(1H, t, H-6), 7.20(1H, d, H-4), 7.16(1H, dd, H-5), 6.80(1H, dd, H-7), 4.05(3H, s, OCH$_3$), 3.58(2H, broad, NH$_2$).

(2) Preparation of 3-hydroxy-8-methoxy quinoline [Compound (V)]

In 53 ml of 33%(v/v) sulfuric acid was dissolved 6.2 g of 3-amino-8-methoxy quinoline [compound (IV)]. The solution was cooled to 0° C., and to the solution was slowly dropped 2.6 g of sodium nitrite which is dissolved in 12 ml of water. The solution was agitated at 0° to 5° C. for 30 minutes. The resulting solution was dropped in 47 ml of 50%(v/v) which was kept 160° C., agitated for 1 hour, and cooled. To the solution was added 300 ml of water and neutralized with aqueous potassium carbonate. By filtering and drying the solid portion, 3.8 g of 3-hydroxy-8-methoxy quinoline [compound (V)], which is yellow-red, was obtained in a solid state.

The spectroscopic property of the compound is as follow: $^1$H-NMR(CDCl$_3$) δ(ppm): 8.65(1H, d, H-2), 7.50(1H, t, H-6), 7.22(1H, dd, H-5), 6.86(1H, dd, H-7), 3.98(3H, s, OCH$_3$).

(3) Preparation of Jineol (3,8-Dihydroxy Quinoline) [Compound (I)]

In 10 ml of dichloromethane was dissolved 175 mg of 3-hydroxy-8-methoxy quinoline [compound (V)]. To the solution was dropped 0.2 ml of boron tribromide 0° to 5° C., and the solution was refluxed for 12 hours. After cooling to room temperature, a small amount of ice was added. To the solution was added 5% aqueous sodium hydroxide, and the solution was agitated at room temperature for 30 minutes. The solution was neutralized with 6N HCl and extracted with ethyl acetate. The resulting extract was washed with water and dried with anhydrous magnesium sulfate. The ethyl acetate was removed by vacuum distillation to obtain 146 mg of jineol (3,8-dihydroxy quinoline) [compound (I)], which is yellow-red, was obtained in a solid state.

The spectroscopic property of the compound is as follow: $^1$H-NMR(CD$_3$OD) δ(ppm): 8.44(1H, d, H-2), 7.41(1H, t, H-4), 7.29(1H, t, H-6), 7.14(1H, dd, H-5), 6.85(1H, dd, H-7).

Example 5

Synthesis of 3,8-Dimethoxy Quinoline 175 mg of 3-hydroxy-8-methoxy quinoline [compound (V)] prepared in example 6 and 66 mg of potassium hydroxide were added to 3 ml of ethanol, and the solution was agitated for 30 minutes. To the solution was added 284 mg of iodomethane, and the solution was agitated for 24 hours. The solvent was removed, and the solution was extracted with dichloromethane. The dichloromethane layer was washed with water and aqueous sodium hydroxide, and dried with anhydrous magnesium sulfate. The dichloromethane was removed by vacuum distillation to give 165 mg of 3,8-dimethoxy quinoline.

The spectroscopic property of the compound is as follow: $^1$H-NMR(CDCl$_3$) δ(ppm): 8.67(1H, d, H-2), 7.42(1H, t, H-6), 7.35(1H, d, H-4), 7.30(1H, dd, H-5), 6.91(1H, dd, H-7), 4.07(3H, s, 8-OCH$_3$), 3.94(3H, s, 3-OCH$_3$); $^1$H-NMR (CD$_3$OD) δ(ppm): 8.67(1H, d, H-2), 7.64(1H, d, H-4), 7.46(1H, t, H-6), 7.38(1H, dd, H-5), 7.02(1H, dd, H-7), 4.02(3H, s, 8-OCH$_3$), 3.95(3H, s, 3-OCH$_3$).

Example 6

Synthesis of 3-Acetoxy-8-Methoxy Quinoline 175 mg of 3-hydroxy-8-methoxy quinoline [compound (V)] prepared in example 6 and 132 mg of triethyl amine were added to 10 ml of dichloromethane. After cooled to 0° C., 0.1 ml of acetyl chloride was slowly added dropwise. The solution was agitated for 1 hour, and water was added to the solution. The solution was extracted with dichloromethane and washed with water. The dichloromethane layer was dried with anhydrous magnesium sulfate. The dichloromethane was removed by vacuum distillation to give 195 mg of 3-acetoxy-8-methoxy quinoline as an oil.

The spectroscopic property of the compound is as follow: $^1$H—NMR(CDCl$_3$) δ(ppm): 8.71(1H, d, H-2), 7.93(1H, t, H-4), 7.49(1H, d, H-6), 7.37(1H, dd, H-5), 7.04(1H, dd, H-7), 4.09(3H, s, 8-OCH$_3$), 2.40(3H, s, 3-OCOCH$_3$).

Further modifications of the invention will be apparent to those skilled in the art and all such modifications are deemed to be with the scope of the invention as defined in the following claims.

What is claimed is:

1. A quinoline compound in substantially pure form which is represented as the following formula (I):

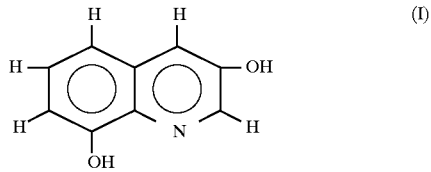

2. A method of extracting the quinoline compound of claim 1, from scolopendra subspinipes which comprises:
   extracting scolopendra subspinipes with a solvent;
   separating an activating portion from the extracted liquid with an organic solvent; and
   purifying an anticancerous activating portion from the activating portion by chromatography.

3. The method according to claim 2 wherein said solvent is methanol or ethanol.

4. The method according to claim 2 wherein said the step of separating comprises:
   a first layer separation for separating the extracts into polar portion and non-polar impurities in an organic solvent; and
   a second layer separation for separating the polar portion into polar impurities and activating portion in an organic solvent.

5. The method according to claim 4 wherein said organic solvent of the first layer separation is hexane or methanol.

6. The method according to claim 4 wherein said organic solvent of the second layer separation is a mixed solution of water and ethyl acetate or a mixed solution of water and chloroform.

7. The method according to claim 2 wherein said chromatography is silicagel chromatography and/or LH-20 chromatography.

8. A quinoline compound, which is represented as the following formula (II):

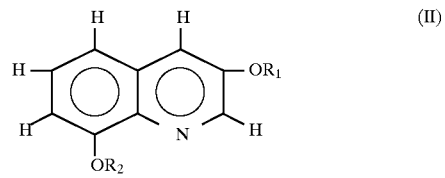

wherein each R$_1$ and R$_2$, independently of each other, is a hydrogen; a lower alkyl group of C$_1$ to C$_8$; a cycloalkyl group of C$_5$ to C$_7$ having a substituting group; an alkyl group of C$_1$ to C$_4$ having a phenyl group with one to three substituting groups; a lower alkyl group of C$_1$ to C$_6$ having a hydroxy, an alkoxy having C$_1$ to C$_5$, or an aryloxy; a lower acyl group of C$_1$ to C$_7$ having a hydroxy, an alkoxy having C$_1$ to C$_5$, or an aryloxy; a cycloalkylcarbonyl group of C$_5$ to C$_7$ with one to three substituting groups; or an acyl group of C$_1$ to C$_4$ having a phenyl group with one to three substituting groups with the proviso that said compound is in substantially pure form when R$_1$ and R$_2$ are both hydrogen.

9. The quinoline compound according to claim 2 wherein said R$_1$ and R$_2$ are methyl groups.

10. The quinoline compound according to claim 2 wherein said R$_1$ and R$_2$ are acetyl groups.

11. A method of preparing 3,8-dimethoxy quinoline, which comprises:
    reacting the quinoline compound of claim 1 with diazomethane.

12. A method of preparing 3,8-diacetoxy quinoline, which comprises:
    reacting the quinoline compound of claim 1 with acetic anhydride.

13. A pharmaceutical composition for anticancer, which comprises:
    a quinoline compound of claim 1, 8, 9 or 10;
    a pharmaceutically acceptable carrier; and
    other pharmaceutically acceptable additives.

14. A method of synthesizing the quinoline compound of the following formula (II) as the following reaction paths, which comprises:
    producing compound (IV) having an amine group by Hoffmann rearrangement of the compound of formula (III);
    producing compound (V) having a hydroxy group through a diazotization of the resultant compound (IV) in an acidic medium; and
    carrying out dealkylation, alkylation or acylation of compound (V):

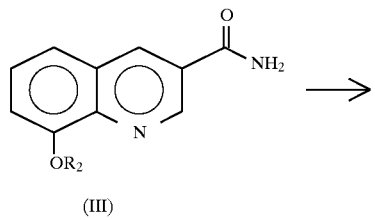

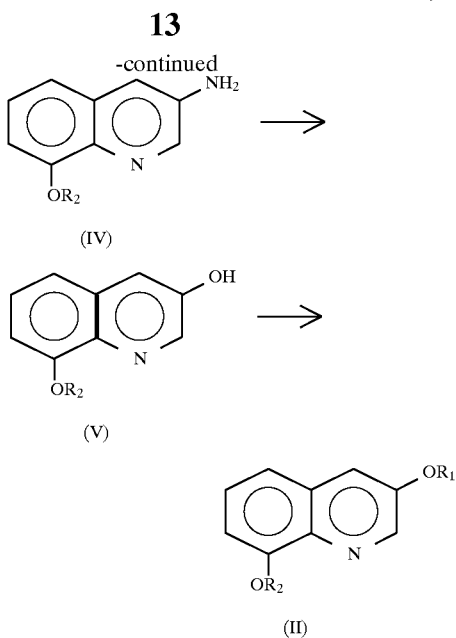

wherein each $R_1$ and $R_2$, independently of each other, is a hydrogen; a lower alkyl group of $C_1$ to $C_6$; a cycloalkyl group of $C_5$ to $C_7$ having a substituting group; an alkyl group of $C_1$ to $C_4$ having a phenyl group with one to three substituting groups; a lower alkyl group of $C_1$ to $C_6$ having a hydroxy, an alkoxy having $C_1$ to $C_5$, or an aryloxy; a lower acyl group of $C_1$ to $C_7$ having a hydroxy, an alkoxy having $C_1$ to $C_5$, or an aryloxy; a cycloalkylcarbonyl group of $C_5$ to $C_7$ with one to three substituting groups; or an acyl group of $C_1$ to $C_4$ having a phenyl group with one to three substituting groups.

15. A method of synthesizing 3,8-dihydroxy quinoline, which comprises:
producing 3-amino-8-methoxy quinoline by Hoffmann rearrangement of 8-methoxy quinoline-3-carboxylamide;
producing 3-hydroxy-8-methoxy quinoline through a diazotization of 3-amino-8-methoxy quinoline in an acidic medium; and
carrying out dealkylation of 3-hydroxy-8-methoxy quinoline.

16. A method of synthesizing 3,8-dimethoxy quinoline, which comprises:
producing 3-amino-8-methoxy quinoline by Hoffmann rearrangement of 8-methoxy quinoline-3-carboxylamide;
producing 3-hydroxy-8-methoxy quinoline through a diazotization of 3-amino-8-methoxy quinoline in an acidic medium; and
carrying out alkylation of 3-hydroxy-8-methoxy quinoline.

17. A method of synthesizing 3,8-diacetoxy quinoline, which comprises:
producing 3-amino-8-methoxy quinoline by Hoffmann rearrangement of 8-methoxy quinoline-3-carboxylamide;
producing 3-hydroxy-8-methoxy quinoline through a diazotization of 3-amino-8-methoxy quinoline in an acidic medium; and
carrying out acylation of 3-hydroxy-8-methoxy quinoline.

18. A method for treating cancer which comprises administering a compound to an animal suffering from cancer, said compound having the formula:

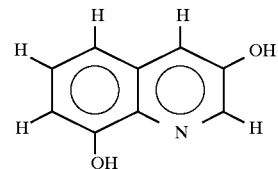

19. A method for treating cancer which comprises administering the compound of claim 8 to an animal suffering from cancer.

20. A method for treating cancer which comprises administering the compound of claim 14 to an animal suffering from cancer.

* * * * *

UNITED STATES PATENT AND TRADEMARK OFFICE
CERTIFICATE OF CORRECTION

PATENT NO. : 5,824,689
DATED : October 20, 1998
INVENTOR(S) : Ho-Seong Lee et al.

It is certified that error appears in the above-indentified patent and that said Letters Patent is hereby corrected as shown below:

Column 12, line 15 the term "$C_1$-$C_8$" should read --$C_1$-$C_6$ --.

Signed and Sealed this

Sixteenth Day of March, 1999

Attest:

Q. TODD DICKINSON

Attesting Officer

Acting Commissioner of Patents and Trademarks